United States Patent [19]

Brich et al.

[11] Patent Number: 4,515,950

[45] Date of Patent: May 7, 1985

[54] PROCESS FOR THE ISOMERIZATION OF ERGOVINE DERIVATIVES

[75] Inventors: Zdenek Brich; Herbert Mühle, both of Binningen, Switzerland

[73] Assignee: Sandoz Ltd., Basel, Switzerland

[21] Appl. No.: 375,290

[22] PCT Filed: Sep. 23, 1981

[86] PCT No.: PCT/CH81/00105

§ 371 Date: Apr. 26, 1982

§ 102(e) Date: Apr. 26, 1982

[30] Foreign Application Priority Data

Sep. 23, 1980 [CH] Switzerland ............... 7122/80

[51] Int. Cl.$^3$ ............................................ C07D 519/02
[52] U.S. Cl. ........................................ 546/67; 546/68; 546/69
[58] Field of Search .................... 546/67, 68, 69

[56] References Cited

U.S. PATENT DOCUMENTS

| | | | |
|---|---|---|---|
| 3,817,988 | 6/1974 | Barton et al. | 424/241 |
| 4,075,212 | 2/1978 | Bach et al. | 546/67 |
| 4,417,051 | 11/1983 | Sawer et al. | 546/67 |

OTHER PUBLICATIONS

House, Herbert, *Modern Synthetic Reactions*, Benjamin/Cummings, Menlo Park, Calif., (1979).

(Abst.) Cerny, 2nd *European Symposium on Organic Chem.* (Preprint), p. 293.

Benes, et al., "Expermization of Esters . . . ", *Czech. Chem. Comm.* [48](1983), pp. 1333–1340.

*Primary Examiner*—Donald G. Daus
*Assistant Examiner*—G. Hendricks
*Attorney, Agent, or Firm*—Gerald D. Sharkin; Robert S. Honor; Thomas O. McGovern

[57] ABSTRACT

The invention concerns a process for the isomerization of ergoline derivatives substituted in the 8β position by an electron withdrawing radical to the corresponding 8α compounds by removal of the proton in the 8α position and by a following, separately effected, protonation.

19 Claims, No Drawings

PROCESS FOR THE ISOMERIZATION OF ERGOVINE DERIVATIVES

The present invention relates to a process for the isomerization of 8β substituted ergolines to produce the corresponding 8α ergolines.

The 8α substituted ergolines correspond to an unnatural series of the ergot alkaloids, and may be produced from the natural 8β substituted ergolines derivatives. An important 8α ergoline is the iso-9,10-dihydrolysergic acid methyl ester. Previously this compound was produced by converting the corresponding 9,10-dihydrolysergic acid methyl ester into the 8,9-ergolene or 7,8-ergolene which was then hydrogenated to give a mixture containing iso-9,10-dihydrolysergic acid methyl ester. This multi-step process proceded in unsatisfactory yields to an often impure compound. It had also been tried to epimerize 9,10-dihydrolysergic acid methyl ester under equilibrium conditions, i.e. in weak basic conditions with sodium methanolate in methanol, whereupon the β-isomer was primarily obtained because the α-isomer is thermodynamically less stable.

It has now been surprisingly found that protonation effected under kinetic conditions of an anion produced by removal of the proton in the 8α position from an 8β-substituted ergoline yields mainly the 8α isomer.

According to the invention 8α-substituted ergolines are produced by producing in a first step an anion of an ergoline substituted by an electron withdrawing group in the 8β position by removing a proton in the 8α position and in a second separately effected step protonating the resultant anion and if necessary converting the resultant 8α-isomer into the desired ergoline.

The ergoline derivatives for use in the isomerisation according to the invention may be ergoline derivatives having an 8β-electron withdrawing group present in nature or also producible by chemical synthesis.

They may bear substituents usual, e.g. in the chemistry of lysergic acid derivatives. Preferably the nitrogen atom in the 1 position is unsubstituted.

As electron withdrawing group in the 8β position there are contemplated all usual radicals which allow the removal of the proton in the 8β-position, e.g. by formation of an enolate, for example the functional radical of an ester, thioester, amide, aldehyde, hydrazide, imine, hydrazone, nitrile or ketone, preferably an ester or amide. The radical may contain aliphatic or aromatic groups.

When the electron withdrawing radical is a functional group of an ester, it corresponds to the formula COOR wherein R is an aliphatic or aromatic hydrocarbyl group, particularly lower alkyl, e.g. methyl. The other above-mentioned functional groups correspond to for example the following groups, alkylthiocarbonyl, arylthiocarbonyl, formyl, cyano, acyl or carbamoyl, hydrazinocarbamoyl, iminomethyl or hydrazinomethyl each of the last four radicals being optionally substituted by alkyl or aryl.

Ergoline derivatives suitable for the isomerisation according to the present invention encompass especially 9,10-dihydrolysergic acid derivatives, e.g. the compounds of formula I,

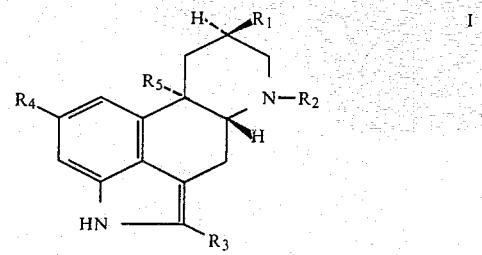

wherein
$R_1$ is an electron withdrawing group,
$R_2$ is alkyl($C_{1-4}$),
$R_3$ is hydrogen, methyl or halogen of atomic number from 9 to 35,
$R_4$ is hydrogen or bromine, and $R_5$ is hydrogen or methoxy.

The conversion of the 8β isomer into the corresponding anion may be effected in known manner under strongly basic conditions e.g. using a non-nucleophilic compound which acts as a strong base under the reaction conditions.

Conveniently a lithium enolate is produced. As base one uses for example lithium dicyclohexylamide, lithium tetramethylpiperide, lithium isopropylcyclohexylamide or preferably lithium diisopropylamide, which may be formed in situ.

Preferably at least one equivalent of base per removable proton is used. Since in the case of an ergoline unsubstituted in the 1 position, the corresponding proton is mainly removed, preferably for production of the dianon at least 2 equivalents of base are used per mole of ergoline. In the case of an ergoline unsubstituted also in the 6 position, 3 equivalents are necessary. Preferably not more than an equivalent excess is used.

The formation of the anion may be effected in an aprotic polar solvent for example in an ether such as tetrahydrofuran. The reaction temperature is conveniently between −110° and +25° C., preferably between −40° and −10° C.

The subsequent protonation of the anion may be effected in known manner by addition of a proton source. As proton source one uses for example water or methanol. Alternatively one can use for example an acid, e.g. acetic acid, hydrochloric acid or tartaric acid, conveniently in an aqueous medium or alternatively in an organic solvent for example in an ether, such as tetrahydrofuran.

The protonation is preferably effected at a low temperature, e.g. below −20° C.

The process according to the invention produces, particularly when the ergoline is unsubstituted in the 1 position, a surprisingly large amount of the 8α substituted ergoline derivative as well as a minor amount of the 8β substituted compound. The 8α isomer may be separated out in conventional manner e.g. by crystallization. If desired the amount of 8β substituted ergoline in the product may be reduced by converting this isomer into another compound if it reacts faster than the 8α isomer. Thus in the case of a mixture of 9,10-dihydrolysergic metyl ester and iso-9,10-dihydrolysergic methyl ester a stoechiometric partial saponification may be effected in the presence of an alkali metal alcoholate and the resultant salt of the 8β isomer can be separated from the 8α isomer, which saponifies slower, in known manner.

The 8α-substituted ergolines produced according to the invention are in general known, pharmacologically active compounds or are valuable intermediates which are suitable for use as starting materials for the production of therapeutically active 8α ergoline derivatives, e.g. 8α-sulfamoylaminoergolines and other 8α-aminoergolines.

For example an ergoline derivative produced according to the invention substituted in the 8α position by a functional radical of an ester may be converted into a corresponding 8α-sulfamoylamino ergoline derivative by treatment of the ester with a mixture of hydrazine hydrate and hydrazine dihydrochloride, conversion of the resultant hydrazide by a Curtius reaction into the corresponding 8α-amino derivative and then by treatment according to known methods, e.g. as described in DOS No. 2 656 344, with a reactive derivative of the corresponding sulfaminic acid. An ergoline derivative produced according to the invention and having a functional radical of an amide, aldehyde, nitrile or imine in the 8α position may be converted in known manner through the free 8α carboxylic acid, e.g. into the methyl ester which may then be converted as described above into the desired 8α-sulfamoylamino derivative.

There may be produced for example 8α-sulfamoylamino derivatives of formula II

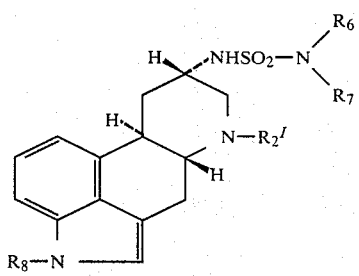

wherein
R$_2^I$ is (C$_{1-4}$)alkyl,
R$_6$ is hydrogen or (C$_{1-3}$)alkyl,
R$_7$ is (C$_{1-4}$)alkyl, and
R$_8$ is hydrogen or methyl.

Such compounds are known from DOS Nos. 2 656 344 and 2 530 577, like e.g. N-(1,6-dimethylergolin-8α-yl)-N,N'-dimethylsulfamide and N-(6-methylergolin-8α-yl)-N,N'-diethylsulfamide.

As compounds of formula II may further be named N'-(6-n-propylergolin-8α-yl)-N,N-diethylsulfamide, N'-(1-methyl-6-n-proylergolin-8α-yl)-N,N-diethylsulfamide, and N-(6-ethylergolin-8α-yl)-N',N'-dimethylsulfamide. These compounds are disclosed in U.S. patent application Ser. No. 286,417 of July 22, 1981, the contents of which are hereby incorporated by reference.

There may also be produced N-ergolinyl-N',N'-diethylurea derivatives of formula III

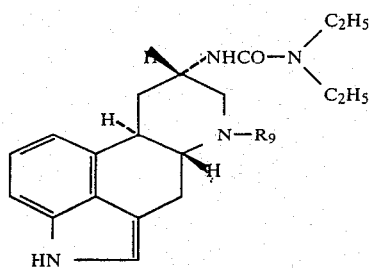

wherein R$_9$ is (C$_{-6}$)alkyl, —(CH$_2$)$_n$—CH=CH$_2$, —(CH$_2$)$_n$—C≡CH, —(CH$_2$)$_n$—COOR', —(CH$_2$)$_n$—CN or

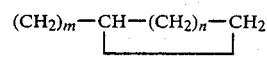

wherein n is 1 or 2 and m is 0 or 1 and R' is (C$_{1-6}$)alkyl.

These compounds are disclosed in European patent application No. 80103177.4.

As examples of compounds of formula III may be named: N-(6-n-propylergolin-8α-yl)-N',N'-diethylurea and N-(6-methylergolin-8α-yl)-N',N'-diethylurea.

The compounds of formulae II and III exhibit in general dopaminergic and prolactin secretion inhibitory activity.

The following example illustrates the invention. Temperature data are in degrees Celsius and are uncorrected.

EXAMPLE

Iso-9,10-dihydrolysergic acid methyl ester

A solution of 72.1 g (0.71 Mol) diisopropylamine in 750 ml tetrahydrofuran is cooled to −30° under argon and is treated dropwise with 308.3 ml (0.66 Mol) n-butyllithium (2.14 Mol in cyclohexane). The resultant solution is stirred thereafter for 30 minutes. A solution of 85.2 g (0.3 Mol) 9,10-dihydrolysergic acid methyl ester in 750 ml tetrahydrofuran is added dropwise. The mixture is then stirred for 30 minutes at −35°.

The hydrolysis is effected by the addition of 384 ml hydrochloric acid (10%; 1.1 Mol) at −30°. The mixture is warmed to room temperature. The organic phase is separated off, dried with magnesium sulphate, and concentrated. The resultant residue weighs 84.3 g (99%) which contains practically only the two possible stereoisomers in a ratio of 85:15. The crude product is purified by crystallization from methylene chloride/hexane (1:2). There is obtained in 75% yield practically pure iso-9,10-dihydrolysergic acid methyl ester, m.pt. 186.9°–187.4° C. The physical properties, spectroscopic data and microanalysis are in agreement with data obtained from iso-9,10-dihydrolysergic acid methyl ester obtained by another method.

The resultant compound may be treated with hydrazine hydrate/hydrazine dihydrochloride in propanol to produce the corresponding hydrazide. The hydrazide may be treated with sodium nitrite in aqueous hydrochloric acid, warmed to 80° and then worked up to give 8α-amino-6-methylergoline. This compound may be optionally methylated in position 1 and acylated with dimethyl or diethyl chlorosulfamide, to give, e.g. N-(1,6-dimethylergolin-8α-yl)-N',N'-dimethylsulfamide or N-(6-methylergolin-8α-yl)-N',N'-diethylsulfamide.

We claim:
1. A process for the production of an 8α-substituted ergoline having an electron withdrawing group as the 8α-substituent which comprises the steps of
   (1) producing an anion of an ergoline having an electron withdrawing substituent in the 8β-position by deprotonating the ergoline under strongly basic conditions with a strong non-nucleophilic lithium amide base and
   (2) thereafter protonating the resultant anion.
2. A process according to claim 1 wherein the ergoline which is deprotonated is unsubstituted in the 1-position.
3. A process according to claim 2 wherein an 8β-ergoline of formula I

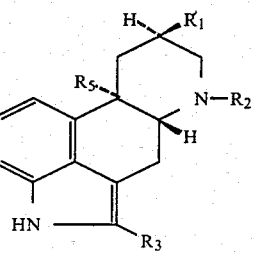

wherein
   $R_1$ is an electron withdrawing group,
   $R_2$ is alkyl($C_{1-4}$),
   $R_3$ is hydrogen, methyl or halogen of atomic weight from 9 to 35,
   $R_4$ is hydrogen or bromine, and
   $R_5$ is hydrogen or methoxy,
is deprotonated under strongly basic conditions with a strong non-nucleophilic lithium amide base and thereafter is protonated to produce the corresponding 8α-ergoline.
4. A process according to claim 1 wherein the electron withdrawing group is a functional radical of an ester, an amide, an aldehyde, a hydrazide, an imine, a nitrile, a hydrazone or a ketone.
5. A process according to claim 1 wherein the anion is a lithium enolate.
6. A process according to claim 1 wherein step 1 is effected in an aprotic polar solvent.
7. A process according to claim 1 in which an 8α-substituted ergoline intermediate is produced and is then converted to the desired 8α-substituted ergoline product.
8. A process according to claim 7 wherein the 8α-substituted ergoline product is an 8α-aminoergoline.
9. A process according to claim 7 wherein the 8α-substituted ergoline product is an 8α-sulphamoylaminoergoline.
10. A process according to claim 7 wherein the 8α-substituted ergoline product is N-(1,6-dimethyl-ergolin-8α-yl)-N',N'-dimethylsulphamide.
11. A process according to claim 7 wherein the 8α-substituted ergoline product is N-(6-methylergolin-8α-yl)-N',N'-diethylsulphamide or N-(6-methylergolin-8α-yl)-N',N'-diethylurea.
12. A process according to claim 1 characterised by the production of N-(6-methylergolin-8α-yl)-N',N'-diethylsulfamide, N'-(1-methyl-6-n-propyoergolin)-8α-yl)- N,N-diethylsulfamide, N-(6-n-propylergolin-8α-yl)-N',N'-diethylurea or N-(6-methylergolin-8α-yl)-N',N'-diethylurea.
13. A process according to claim 3 in which $R_1$ is —COOR, where R is lower alkyl.
14. A process according to claim 13 in which R is $CH_3$.
15. A process according to claim 3 in which the ergoline of formula I is deprotonated with lithium dicyclohexylamide, lithium tetramethylpiperidide, lithium isopropylcyclohexylamide or lithium diisopropylamide.
16. A process according to claim 15 in which the ergoline of formula I is deprotonated in an aprotic polar solvent at a temperature of between $-110°$ and $+25°$ C.
17. A process according to claim 3 in which the deprotonated ergoline is protonated with water, methanol, hydrochloric acid, acetic acid or tartaric acid.
18. A process according to claim 17 in which the ergoline is protonated in tetrahydrofuran or aqueous tetrahydrofuran below $-20°$ C.
19. A process according to claim 1 in which an 8β-ergoline of the formula

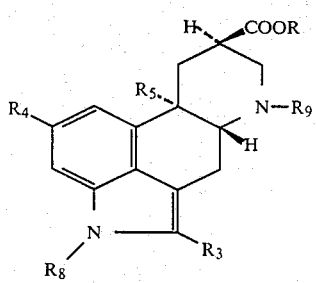

wherein
   R is lower alkyl,
   $R_3$ is hydrogen, methyl or halogen of atomic weight from 9 to 35,
   $R_4$ is hydrogen or bromine,
   $R_5$ is hydrogen or methoxy,
   $R_8$ is hydrogen or methyl,
   $R_9$ is $(C_{1-6})$alkyl, $-(CH_2)_n-CH=CH_2$, $-(CH_2)_n-C\equiv CH$, $-(CH_2)_n-COOR'$, $-(CH_2)_n-CN$ or

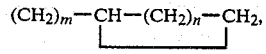

n is 1 or 2,
m is 0 or 1, and
R' is $(C_{1-6})$alkyl
is deprotonated in an aprotic polar solvent at a temperature between $-110°$ and $+25°$ C. with a non-nucleophilic base selected from lithium dicyclohexylamide, lithium tetramethylpiperidide, lithium isopropylcyclohexylamide and lithium diisopropylamide to produce an anion of the 8β-ergoline, and thereafter protonating the anion in tetrahydrofuran or aqueous tetrahydrofuran at a temperature below $-20°$ C. with water, methanol, hydrochloric acid, acetic acid or tartaric acid to produce the corresponding 8α-ergoline.

* * * * *